(12) United States Patent
Corbin et al.

(10) Patent No.: US 7,618,672 B2
(45) Date of Patent: Nov. 17, 2009

(54) SELECTIVE REMOVAL OF OLIGOSACCHARIDES FROM AQUEOUS MIXTURES USING ZEOLITES

(75) Inventors: David Richard Corbin, West Chester, PA (US); Vasantha Nagarajan, Wilmington, DE (US); Vidya Pai, Wilmington, DE (US); Stuart M. Thomas, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 771 days.

(21) Appl. No.: 10/983,316

(22) Filed: Nov. 5, 2004

(65) Prior Publication Data
US 2005/0202141 A1 Sep. 15, 2005

Related U.S. Application Data

(60) Provisional application No. 60/517,770, filed on Nov. 5, 2003.

(51) Int. Cl.
| A23L 1/20 | (2006.01) |
| A23L 1/36 | (2006.01) |
| A23L 2/00 | (2006.01) |
| A61K 36/48 | (2006.01) |
| C01B 33/36 | (2006.01) |
| C13J 1/06 | (2006.01) |

(52) U.S. Cl. ............... 426/634; 423/713; 423/DIG. 21; 424/757; 426/590; 426/629; 127/46.2
(58) Field of Classification Search .................. 426/634, 426/629
See application file for complete search history.

(56) References Cited

U.S. PATENT DOCUMENTS

| 3,308,069 | A | * | 3/1967 | Rosinski et al. ............... 502/62 |
| 5,482,631 | A | * | 1/1996 | Saska et al. .................. 210/635 |
| 5,972,995 | A | | 10/1999 | Fischer et al. |
| 6,521,208 | B1 | * | 2/2003 | Cooper et al. ............... 423/713 |
| 6,663,805 | B1 | * | 12/2003 | Ekiner et al. ............... 264/45.9 |
| 6,797,309 | B2 | * | 9/2004 | Monagle ..................... 426/590 |
| 2002/0119208 | A1 | * | 8/2002 | Chajuss ....................... 424/757 |

FOREIGN PATENT DOCUMENTS

| GB | 1585369 | * | 3/1981 |
| JP | 7-28227 | | 3/1995 |
| KR | 10-2000-0055133 | * | 9/2000 |
| KR | 2000-0055133 | | 9/2000 |

OTHER PUBLICATIONS

English translation of KR10-2000-0055133 (see above).*
EPA, Technical Bulletin, Zeolite a Versatile Air Pollutant Adsorber (1998).*
John D. Sherman et al., Carbohydrate Separations Using Zeolite Molecular Sieves, Stud. Surf. Sci. Catal., vol. 28:1025-1032, 1980.

(Continued)

*Primary Examiner*—David R Sample
*Assistant Examiner*—Brent T O'Hern

(57) ABSTRACT

The present invention relates to a process for selectively removing undesired oligosaccharides from aqueous mixtures such as plant processing waste products, including soy whey and other vegetable wheys, using an ultrastabilized large pore, hydrophobic zeolite Y. The resulting solution, which contains isoflavones and digestible sugars such as glucose, fructose and sucrose, can serve as the basis for a nutritious new product.

8 Claims, 3 Drawing Sheets

OTHER PUBLICATIONS

Shigemitsu Kudou et al., Malonyl Isoflavone Glycosides in Soybean Seeds, Agric. Biol. Chem., vol. 55:2227-2233, 1991.

Christoph Buttersack et al., High Specific Interaction of Polymers with the Pores of Hydrophobic Zeolites, Langmuir, vol. 12(13):3102-3106, 1996.

Christoph Buttersack et al., Specific Adsorption of Saccharides by Dealuminated Y-Zeolites, J. Phys. Chem., vol. 97:11861-11864, 1993.

Yasuhito Matsubara et al., Recovery of Oligosaccharides from Steamed Soybean Waste Water in Tofu Processing by Reverse Osmosis and Nanofiltration Membranes, Biosci. Biotech. Biochem., vol. 60(3):421-428, 1996.

Cecilia Ho et al., A Comparative Study of Zeolite and Resin Adsorbents for the Separation of Fructose-Glucose Mixtures, Ind. Eng. Chem. Res., vol. 26:1407-1412, 1987.

\* cited by examiner

SELECTIVE REMOVAL OF OLIGOSACCHARIDES FROM AQUEOUS MIXTURES USING ZEOLITES

FIELD OF THE INVENTION

The present invention relates to a process for selectively removing oligosaccharides from aqueous mixtures. More specifically, the invention involves the use of an ultrastabilized, hydrophobic zeolite Y to remove undesired oligosaccharides, such as raffinose and stachyose, from plant processing waste products, such as soy whey, to give a nutritious product containing isoflavones and digestible sugars.

BACKGROUND OF THE INVENTION

Isoflavones are crystalline ketones found primarily in leguminous plants. One of the most important sources of isoflavones is the soybean, which contains twelve distinct isoflavones: genistein, genistin, 6"-O-malonylgenistin, 6"-O-acetylgenistin, daidzein, daidzin, 6"-O-malonyldaidzin, 6"-O-acetyldaidzin, glycitein, glycitin, 6"-O-malonylglycitin, 6"-O-acetylglycitin (Kudou, *Agric. Biol. Chem.* 55, 2227-2233, 1991). These soybean isoflavones share the generic structure shown below:

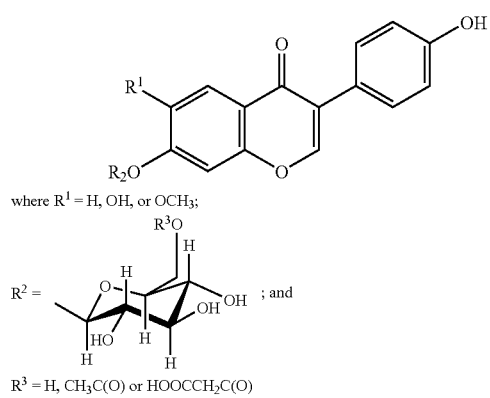

where $R^1$ = H, OH, or $OCH_3$;

$R^2$ = [structure shown]; and $R^3$ = H, $CH_3C(O)$ or $HOOCCH_2C(O)$

Dietary isoflavones are believed to have health benefits. For example, they are believed to be responsible for the cholesterol-lowering effect of soy products, and may help prevent breast cancer. Moreover, isoflavones are believed to ameliorate menopausal symptoms. U.S. Pat. No. 5,972,995 teaches the treatment of cystic fibrosis patients by administering isoflavones capable to stimulate chloride transport.

Soy protein isolates are typically prepared from defatted soy meal. Proteins and soluble carbohydrates are extracted into aqueous solution (pH 7-10). The insoluble residue is mostly fiber and is removed by centrifugation. The protein is precipitated from solution as curd at its isoelectric point (about pH 4.5), further purified, neutralized, and dried. The liquid remaining after the protein has been isolated is referred to as whey and contains mainly soluble carbohydrates. Most of the isoflavones are retrieved with the protein curd.

Isoflavones also exist at the parts per million (ppm) level in the whey. Soy whey also contains carbohydrates, primarily sugars such as the monosaccharides glucose and fructose and the oligosaccharides sucrose (disaccharide), raffinose (trisaccharide) and stachyose (tetrasaccharide), in addition to proteins, salts and other bioactives. The oligosaccharides raffinose and stachyose require the enzyme α-galactosidase, which is not present in the human gastrointestinal tract, to be completely hydrolyzed into monosaccharides that can be absorbed into the blood stream. The unhydrolyzed oligosaccharides pass into the large intestine where they are fermented by anaerobic microorganisms producing gases such as $CO_2$, $H_2$, and $CH_4$ that lead to flatulence. Currently, the soy whey is treated as waste with significant disposal costs. The selective removal of these undesirable oligosaccharides from soy whey would yield new, nutritious food products.

Methods for the removal of oligosaccharides from soybean wastes are known in the art. For example, Matsubara et al [*Biosci. Biotech. Biochem.* 60:421 (1996)] describe a method for recovering soybean oligosaccharides from steamed soybean wastewater using reverse osmosis and nanofiltration membranes.

JP 07-082,287 teaches the recovery of oligosaccharides from soybean oligosaccharide syrup using solvent extraction. The method comprises adding an organic solvent to the aqueous solution containing the oligosaccharides, heating the mixture to give a homogeneous solution, cooling the solution to form two liquid layers, and separating and recovering the bottom layer. KR 2000/055133 describe a method for separating oligosaccharides from bean curd waste solution. In that method, the waste solution is passed through a polymeric resin column to remove saponin and isoflavone. Then, the waste solution that passed through the column is filtered and concentrated to recover the oligosaccharides.

In all these disclosures, the undesirable oligosaccharides raffinose and stachyose are recovered along with the desirable sugars, sucrose, glucose, and fructose. There have been no reports of a method for selectively removing the undesired oligosaccharides raffinose and stachyose from plant processing waste products such as soy whey to obtain a nutritious product containing isoflavones, and digestible sugars, such as glucose, fructose, and sucrose.

Zeolites are high capacity, selective adsorbents that have been widely used for the separation of a variety of chemical compounds. Zeolites can be generically described as complex aluminosilicates characterized by three-dimensional framework structures enclosing cavities occupied by ions and water molecules, all of which can move with significant freedom within the zeolite matrix (Meier et al, *Atlas of Zeolite Structure Types*, Elsevier, 2001). In commercially useful zeolites, the water molecules can be removed from or replaced within the framework structures without destroying the zeolite's geometry.

Zeolites have been widely used as bulk adsorbents and as chromatography supports for separating a variety of substances including gases, hydrocarbons, and alcohols. The use of zeolites as selective adsorbents for carbohydrates is particularly well known in the art. For example, the use of zeolites for the separation of monosaccharides is described by Ho et al [*Ind. Eng. Chem. Res.* 26:1407 (1987)], and Sherman et al [*Stud. Surf. Sci. Catal.* 28:1025 (1980)]. Additionally, a process for separating monosaccharides using zeolite adsorbents is described in U.S. Pat. Nos. 4,405,377 and 4,483,980. The adsorption selectivity of the zeolites to monosaccharides is determined by the extent of interaction with the cations present in the zeolite, as well as the geometric constraints imposed by the zeolite pore geometries and cation positions, as discussed by Sherman et al [*Stud. Surf. Sci. Catal.* 28:1025 (1980)].

Buttersack et al [*J. Phys. Chem.* 97:11861 (1993)] report that the dealumination of Y-zeolites enhance their affinity to mono-, di-, and trisaccharides by hydrophobic interactions. The adsorption of oligosaccharides such as raffinose and stachyose by a hydrophobic zeolite, specifically, dealuminated FAU type zeolite (Si/Al=110), is described by Buttersack et al [*Langmuir* 12:3101 (1996)]. The FAU type zeolite used in that investigation was sold by Degussa Company, South Plainfield, N.J., under the product name Wessalith® DAY-55. That disclosure reports that DAY-55 has a very strong affinity for stachyose, a strong affinity for raffinose and sucrose, and very little affinity for glucose when tested in a single component system. The adsorption characteristics of this zeolite were not tested in a multi-component system consisting of a mixture of sugars.

There remains a need for a simple, economical process to remove undesirable oligosaccharides such as raffinose and stachyose from biological or plant processing waste products such as soy whey and other vegetable wheys to give a nutritious product containing isoflavones and digestible sugars, such as glucose, fructose, and sucrose. The adsorbent for this purpose must have a high selectivity for raffinose and stachyose in the presence of the digestible sugars and other components of the whey.

SUMMARY OF THE INVENTION

One embodiment of this invention is a method for selectively removing the oligosaccharides raffinose and stachyose from an aqueous mixture by:
(a) contacting the aqueous mixture with an ultrastabilized hydrophobic zeolite Y having a Si/Al ratio of about 10 to about 45;
(b) separating the zeolite from the aqueous mixture; and
(c) recovering the aqueous mixture.

A further embodiment of this invention is a method of using an ultrastabilized hydrophobic zeolite Y having a Si/Al ratio of about 10 to about 45 for selectively removing the oligosaccharides raffinose and stachyose from an aqueous mixture by:
(a) contacting the aqueous mixture with said ultrastabilized zeolite;
(b) separating the zeolite from the aqueous mixture; and
(c) recovering the aqueous mixture Yet another embodiment of this invention is a vegetable whey containing glucose in an amount of at least about 50 ppm, raffinose in an amount of no more than about 400 ppm, and stachyose in an amount of no more than about 500 ppm.

Yet another embodiment of this invention is a vegetable whey containing fructose in an amount of at least about 10 ppm, raffinose in an amount of no more than about 400 ppm, and stachyose in an amount of no more than about 500 ppm.

Yet another embodiment of this invention is a vegetable whey containing sucrose in an amount of at least about 500 ppm, raffinose in an amount of no more than about 400 ppm, and stachyose in an amount of no more than about 500 ppm.

DETAILED DESCRIPTION OF THE INVENTION

Figure 1:
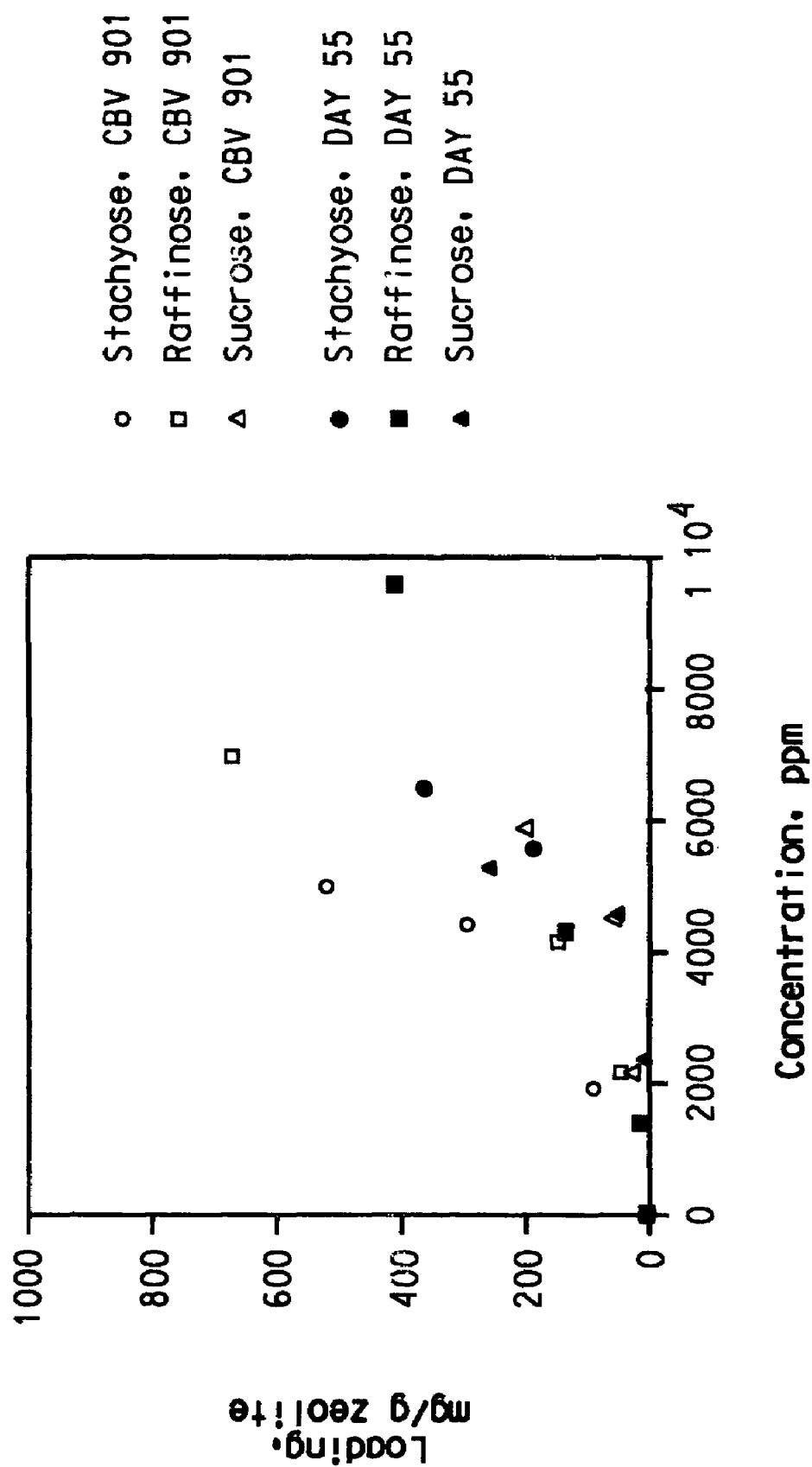
FIG. 1 shows the adsorption of sugars from single sugar solutions by the zeolites CBV-901 and DAY-55.

This invention involves the use of an ultrastabilized, hydrophobic zeolite Y, such as the zeolites CBV-901 (available from Zeolyst, Valley Forge, Pa.) and HiSiv™ 4000 (available from UOP, Des Plaines, Ill.) to adsorb raffinose and stachyose. These zeolites have improved selectivity for larger oligosaccharides over monosaccharides and disaccharides in multi-component systems, compared to other zeolites disclosed in the art. The use of these zeolites enables the selective removal of raffinose and stachyose from aqueous mixtures such as plant processing waste products, including soy whey and other vegetable wheys, to yield a nutritious product containing isoflavones and digestible sugars such as glucose, fructose and sucrose. The process involves contacting the aqueous mixture containing the undesired oligosaccharides with an ultrastabilized, hydrophobic zeolite Y, such as zeolite CBV-901 or HiSiv™ 4000. The zeolite is removed and the aqueous mixture is recovered and used as the basis for a nutritious product.

Various abbreviations as used herein may be defined as follows:
AFI refers to the zeolite structure type $AlPO_4$-5
BEA refers to zeolite beta.
C is equilibrium isoflavone concentration in units of mg/L.
CHA refers to the zeolite structure type Chabazite.
ERI refers to the zeolite structure type Erionite.
FAU refers to the zeolite faujasite.
FER refers to the zeolite structure type Ferrierite.
GIS refers to the zeolite structure type Gismondine.
h is hour or hours.
HPLC refers to the separation and analysis technique, high performance liquid chromatography.
IC is ion chromatography.
KDa means kilodaltons.
KFI refers to the zeolite structure type ZK-5.
LTA refers to the zeolite structure type Linde Type A.
LTL refers to the zeolite structure type Linde Type L.
mM is a unit of concentration meaning millimoles per liter.
MEL refers to the zeolite structure type ZSM-11.
MFI refers to the zeolite structure type ZSM-5.
MOR refers to the zeolite mordenite.
nm is nanometers.
ppm is a unit of concentration meaning parts per million.
PS-DVB refers to a poly(styrene-co-divinylbenzene) adsorbent.
MW is molecular weight.
rpm is revolutions per minute.
RHO refers to the zeolite structure type Rho.
TON refers to the zeolite structure type Theta-1.

The process of this invention is applicable to an aqueous mixture including, but not limited to, plant processing waste products. Plant processing waste products are herein defined as any waste product resulting from the processing of plant material, especially wastes from leguminous plants, such as soy beans, peanuts, and many bean species including mung beans, pigeon peas, and chick peas. These plant processing wastes contain a mixture of sugars including monosaccharides, disaccharides, and higher oligosaccharides.

The term "monosaccharide" will herein refer to simple sugars composed of one sugar unit, for example, glucose and fructose. "Disaccharide" will refer to a sugar consisting of two sugar units, for example sucrose. "Oligosaccharide" will refer to sugars consisting of between 2 and 10 sugar units. Raffinose is a trisaccharide consisting of fructose, glucose and galactose units. Stachyose is a tetrasaccharide consisting of fructose, glucose, and two galactose units. The term "isoflavones" will herein refer to a class of crystalline ketones found in leguminous plants that are believed to have numerous health benefits. These include, but are not limited to, the soy isoflavones: genistein, genistin, 6"-O-malonylgenistin, 6"-O-acetylgenistin, daidzein, daidzin, 6"-O-malonyldaidzin, 6"-O-acetyldaidzin, glycitein, glycitin, 6"-O-malonylglycitin, 6"-O-acetylglycitin. The aqueous mixture can be in the form of a homogeneous solution, a heterogeneous suspension, or an emulsion.

The material to which the process of this invention is applied is preferably soy whey. Soy whey is a by-product of soybean processing, which is reviewed in *Soybeans—Chemistry, Technology, and Utilization*, by KeShun Liu (Chapman & Hall, New York, 1997). The processing of soybeans may be done in many well-known ways. For example, soy protein isolates are typically prepared from defatted soy meal. Proteins and soluble carbohydrates are extracted into aqueous solution (pH 7-10). The insoluble residue is mostly fiber and is removed by centrifugation. The protein is precipitated from solution as curd at its isoelectric point (about pH 4.5).

The liquid remaining after the protein has been isolated is referred to as the soy whey, which is typically treated as waste. The whey contains isoflavones at the parts per million (ppm) level, as well as soluble carbohydrates, primarily sugars such as the monosaccharides glucose and fructose and the oligosaccharides sucrose (disaccharide), raffinose (trisaccharide) and stachyose (tetrasaccharide). It is desirable to selectively remove the undesired oligosaccharides raffinose and stachyose, which are not readily digested in the human gastrointestinal tract, from the whey to yield a nutritious product containing isoflavones and digestible sugars such as glucose, fructose, and sucrose.

The aqueous mixture is treated to remove particulate matter by means including, but not limited to, filtration or centrifugation. For example, the aqueous mixture may be ultrafiltered through a 10 KDa hollow fiber module. Then the treated sample may be contacted with the calcined zeolite adsorbent in the form of a batch reactor, a fluidized bed reactor or a packed column. Separation methods such as these are well known in the art. For example, the use of batch reactors and fluidized bed reactors is described in U.S. Pat. No. 4,483,980, incorporated herein by reference. The use of adsorption resins in a packed column is described in U.S. Pat. No. 6,033,714, incorporated herein by reference.

Methods for calcining zeolites are well known in the art (Shannon et al., *J. Catal.* 113:367-382 (1988)). One example is to heat the zeolite in air at a rate of 1° C./minute to 400° C., holding for 10 minutes at 400° C., heating to 450° C. at a rate of 1° C./minute, holding for 10 minutes at 450° C., heating to 500° C. at a rate of 1° C./minute, holding at 500° C. for 5 hours, then cooling to 110° C.

Zeolites can be generally represented by the following formula: $M_{2/n}O.Al_2O_3.xSiO_2.yH_2O$; wherein M is a cation of valence n, x is greater than or equal to 2, and y is a number determined by the porosity and the hydration state of the zeolite, generally from 2 to 8. In naturally occurring zeolites, M is principally represented by Na, Ca, K, Mg and Ba in proportions usually reflecting their approximate geochemical abundance. The cations M are loosely bound to the structure and can frequently be completely or partially replaced with other cations by conventional ion exchange.

The zeolite framework structure has corner-linked tetrahedra with Al or Si atoms at centers of the tetrahedra and oxygen atoms at the corners. Such tetrahedra are combined in a well-defined repeating structure comprising various combinations of 4-, 6-, 8-, 10-, and 12-membered rings. The resulting framework structure is one of regular channels and cages, which has a pore network that is useful for separation. Pore dimensions are determined by the geometry of the aluminosilicate tetrahedra forming the zeolite channels or cages, with nominal openings of about 0.26 nm for 6-member rings, about 0.40 nm for 8-member rings, about 0.55 nm for 10-member rings and about 0.74 nm for 12-member rings (these numbers assume ionic radii for oxygen). Zeolites with the largest pores, being 8-member rings, 10-member rings, and 12-member rings, are considered small, medium, and large pore zeolites, respectively. Pore dimensions are critical to the performance of these materials in catalytic and separation applications, since this characteristic determines whether molecules of certain size can enter and exit the zeolite framework. In practice, it has been observed that very slight decreases in ring dimensions can effectively hinder or block movement of particular molecular species through the zeolite structure.

The effective pore dimensions that control access to the interior of the zeolites are determined not only by the geometric dimensions of the tetrahedra forming the pore opening, but also by the presence or absence of ions in or near the pore. For example, in the case of zeolite type A, access can be restricted by monovalent ions, such as $Na^+$ or $K^+$, which are situated in or near 8-member ring openings as well as 6-member ring openings. Access can be enhanced by divalent ions, such as $Ca^{2+}$, which are situated only in or near 6-member ring openings. Thus, the potassium and sodium salts of zeolite A exhibit effective pore openings of about 0.3 nm and 0.4 nm respectively, whereas the calcium salt of zeolite A has an effective pore opening of 0.5 nm. The presence or absence of ions in or near the pores, channels, and/or cages can also significantly modify the accessible pore volume of the zeolite for sorbing materials.

Representative examples of zeolites are small pore zeolites such as NaA (LTA), CaA (LTA), Erionite (ERI), Rho (RHO), ZK-5 (KFI) and chabazite (CHA); medium pore zeolites such as ZSM-5 (MFI), ZSM-11 (MEL), ZSM-22 (TON), and ZSM-48; and large pore zeolites such as zeolite beta (BEA), faujasite (FAU), mordenite (MOR), zeolite L (LTL), NaX (FAU), NaY (FAU), DA-Y (FAU) and CaY (FAU). The letters in parentheses give the framework structure type of the zeolite.

Hydrophobic zeolites generally have Si/Al ratios greater than or equal to about 5 and the hydrophobicity generally increases with increasing Si/Al ratios. The presence of aluminum atoms in the zeolite frameworks results in hydrophilic sites. On removal of these framework aluminum atoms, water adsorption is seen to decrease and the material becomes more hydrophobic and generally more organophilic. See for example the discussion of hydrophobicity in zeolites by Chen [*J. Phys. Chem.* 80:60 (1976)].

Zeolites with a high Si/Al ratio can be prepared synthetically or by modification of high alumina-containing zeolites using methods well known in the art. These methods include treatment with $SiCl_4$ or $(NH_4)_2SiF_6$ to replace Al with Si, as well as thermal treatment using steam, followed by acid treatment. A $SiCl_4$ treatment is described by Blatter et al. (*J. Chem. Ed.* 67: 519 (1990)). An $(NH_4)_2SiF_6$ treatment is described in U.S. Pat. No. 4,503,023. A thermal treatment with steam, followed by acid treatment procedure is described in U.S. Pat. No. 3,506,400. Zeolites prepared using this thermal treatment are herein referred to as "ultrastabilized zeolites". All of these treatments are generally very effective at increasing the Si/Al ratio for zeolites such as zeolites Y and mordenite. In addition, WO 00/51940 describes a method for preparing a more hydrophobic, ultrastabilized zeolite with a high Si/Al ratio by thermal treatment comprising calcining zeolite Y in steam under turbulent conditions with respect to the flow pattern of the zeolite at a temperature between 650-1000° C.

Without wishing to be bound by any theory, ultrastabilized, hydrophobic zeolite Y may have a significantly higher affinity for the oligosaccharides raffinose and stachyose in mixtures containing other sugars than hydrophobic zeolites prepared by treatment with $SiCl_4$ or $(NH_4)_2SiF_6$, such as zeolite Wessalith® DAY-55, because the thermal treatment of zeolites to make them more hydrophobic can result in the substantial removal of cations such as $H^+$ and $NH_4^+$ from their normal association with $AlO_4^-$ tetrahedra. This creates an electrovalent imbalance in the zeolite structure [as noted, for example, in U.S. Pat. No. 4,503,023; and Szostak in *Introduction to Zeolite Science and Practice* (Bekkum et al eds) Studies in Surface Science and Catalysis, Vol 58, Elsevier, New York, 1991, Chapter 5], and this imbalance must be accompanied by structural rearrangement in the zeolite to restore the electrovalent balance, which results in significantly different properties. Zeolites that are treated with $SiCl_4$ or $(NH_4)_2SiF_6$ to make them more hydrophobic do not undergo the structural changes that are inherent with the thermal treatments. This structural difference may explain the different behavior of the hydrophobic zeolites with respect to oligosaccharide adsorption.

A particularly suitable zeolite for use in this invention is consequently ultrastabilized, hydrophobic zeolite Y having a Si/Al ratio of about 10 to about 45. Y zeolites are large pore zeolites, having the faujasite framework structure. The ultrastabilized, hydrophobic zeolite Y may be prepared by the process of thermal treatment with steam followed by acid treatment, as described in U.S. Pat. No. 3,506,40, which is incorporated in its entirety as a part hereof for all purposes. The starting material for this procedure may be zeolite NaY [which is available commercially from various sources such as Alfa (Milwaukee, Wis.)] that is either ammonium- or hydrogen-exchanged. Alternatively, the ultrastabilized, hydrophobic zeolite Y may be prepared by the thermal method described in WO 00/51940, which is incorporated in its entirety as a part hereof for all purposes. In that procedure the ultrastabilized, hydrophobic zeolite Y is prepared by calcining zeolite Y with steam under turbulent conditions with respect to flow pattern of the zeolite. Turbulent conditions refer to a condition wherein the gas flows through the dispersed solid phase without a discernable interface. Examples of ultrastabilized, hydrophobic Y zeolites suitable for use in the present invention that are available commercially include, but are not limited to, zeolite CBV-901 (available from Zeolyst, Valley Forge, Pa.) and HiSiv™ 4000 (available from UOP, Des Plaines, Ill.).

As shown in Examples 1, 4 and 5, the ultrastabilized, hydrophobic Y zeolites used in the present invention were found surprisingly to have a significantly higher affinity for the oligosaccharides raffinose and stachyose in mixtures containing other sugars than other zeolites reported in the art, including zeolite Wessalith® DAY-55.

Following contact of the aqueous mixture with the zeolite adsorbent, the adsorbent is separated from the aqueous mixture. When the zeolite is used in a batch reactor, this separation can be accomplished by means that include, but are not limited to, filtration or centrifugation. When the zeolite is used in a column, the separation occurs by passing the aqueous mixture through the column. The aqueous mixture is recovered and used as the basis for a nutritious new product, containing isoflavones and digestible sugars, which is the product of this invention. This product may be, for example, a vegetable whey, such as a soy whey, that contains one or more of glucose, fructose, sucrose, raffinose and stachyose in the following amounts (in ppm by weight):

glucose in an amount of at least about 50 ppm, or at least about 75 ppm, or at least about 100 ppm, but less than about 10000 ppm;

fructose in an amount of at least about 10 ppm, or at least about 25 ppm, or at least about 50 ppm, but less than about 5000 ppm;

sucrose in an amount of at least about 500 ppm, or at least about 1500 ppm, or at least about 3000 ppm, but less than about 50000 ppm;

raffinose in an amount of no more than about 400 ppm, or no more than about 300 ppm, or no more than about 200 ppm;

stachyose in an amount of no more than about 500 ppm, or no more than about 300 ppm, or no more than about 200 ppm.

Preferably substantially all, or more preferably all, of the raffinose and stachyose is removed from the aqueous mixture.

The adsorbed oligosaccharides may be recovered by treating the zeolite with a suitable solvent to elute them. Suitable solvents include, but are not limited to alcohols such as methanol and ethanol. After recovery, the oligosaccharides may be treated with an enzyme such as α-galactosidase to hydrolyze them into simple sugars. Alternatively, the adsorbed oligosaccharides may be burned off the zeolite so that the zeolite can be reused. For example, the zeolite may be calcined at about 550 to 650° C. in air or oxygen to burn off the oligosaccharides. The zeolite is then ready for reuse.

Methods and materials for use in removing undesirable oligosaccharides such as raffinose and stachyose from aqueous mixtures are also set forth in U.S. application Ser. No. 10/983,125, which is assigned to E. I. du Pont de Nemours and Company and is filed on the same day as this application, and which is incorporated in its entirety as a part hereof for all purposes.

The present invention is further defined in the following examples. These examples, while indicating the preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various uses and conditions.

EXAMPLES

General Methods

Soy Whey Sample Preparation:

Soy whey samples were obtained from DuPont Protein Technologies (St. Louis, Mo.) in the form of soy molasses, consisting of 55% solids. The soy molasses was diluted by mixing one part molasses with 9 parts of deionized water and this mixture was allowed to equilibrate for 90 min. The mixture was then centrifuged at 9000 rpm for 30 min at room temperature. The supernatant from the centrifugation step was used as the soy whey concentrate. The soy whey concentrate was ultra-filtered through a 10 kDA hollow fiber module (UFP-10-E-4A, obtained from A/G Technology Corporation, Needham, Mass.) in batch mode. The soy whey concentrate was pumped and recirculated through the lumen of the hollow fibers in the cartridge using a Masterflex® pump (Cole-Parmer Instruments, Vernon Hills, Ill.). The flow rate of the soy whey concentrate varied from 1 to 5 mL/min. The soy whey permeate from the filter module was collected and either used immediately or was refrigerated for future use. Alternatively, the collected, soy whey permeate was frozen in small batches for future use. Typically, 400-600 mL of soy whey permeate was collected from the ultra-filtration process over a 4 h interval from 1 L of initial soy whey concentrate.

The soy whey permeate was diluted 1:1 with deionized water to generate a sample of soy whey, similar in composition to the expected discharge from the curd washing step. The sugar concentrations in the soy whey samples were determined using ion chromatography as described below.

Quantitation of Sugars Using Ion Chromatography

Sugar concentrations were determined using a Dionex DX500 Ion Chromatograph equipped with a CarboPac PA10 column (Dionex Corp., Sunnyvale, Calif.). The chromatographic separations were carried out at 35° C. using a mobile phase consisting of NaOH (27% of a 200 mM solution) and deionized water (73%) at a flow rate of 1 mL/min. The sugars (glucose, sucrose, fructose, raffinose and stachyose) were detected using an ED Amperometer. The sugars were identified and quantified by comparison to known standards. The sugar concentrations of the original soy whey samples are given in Table 1. Any negative values in the results presented in the following tables should be interpreted as being equal to zero within the experimental error of the measurement.

TABLE 1

Sugar Concentrations of Soy Whey Samples.

| Whey Solution | Glucose (ppm) | Fructose (ppm) | Sucrose (ppm) | Raffinose (ppm) | Stachyose (ppm) |
| --- | --- | --- | --- | --- | --- |
| 1 | 54 | Not measured | 732 | 2175 | Not measured |
| 2 | 86 | 48 | 3019 | 766 | 3153 |
| 3 | 112 | 77 | 3055 | 836 | 3219 |
| 4 | 111 | 78 | 3061 | 797 | 3075 |
| 5 | 98 | 42 | 2524 | 700 | 2963 |
| 6 | 89 | 0 | 1989 | 611 | 2717 |
| 7 | 58 | 11 | 2120 | 394 | 1966 |

Example 1

Screening of Various Zeolites for Selective Adsorption of Sugars

The purpose of this Example was to test a variety of zeolites for the selective adsorption of raffinose and stachyose from dilute soy whey.

Approximately 5 g of each of the zeolite samples listed in Table 2 was calcined in air by raising the temperature 1° C./min to 450° C., holding for 10 min, then raising the temperature 1° C./min to 500° C., holding for 10 min, and finally raising the temperature 1° C./min to 550° C. and holding for 5 h.

TABLE 2

List of Zeolite Samples Used and Their Source

| Sample | Vendor | Product Name | Zeolite Framework | Form | Lot Number |
| --- | --- | --- | --- | --- | --- |
| 1 | PQ[1] | Zeolite P | GIS | Powder | 1643-70 |
| 2 | UOP[2] | S-115 | MFI | Powder | 5676-50 |
| 3 | UOP[2] | HiSiv-3000 | unknown | Powder | 917796060009 |
| 4 | Engelhard[3] | EZ-500 | FER | Powder | 29835 |
| 5 | Zeolyst[1] | CBV-90A | MOR | Powder | 1822-60-30 |
| 6 | Zeolyst[1] | ZD-96081 | MOR | Powder | 2061-57-1 |
| 7 | Chemie Uetikon[4] | Zeocat L | LTL | Powder | 109 |
| 8 | Zeolyst[1] | CP 811 E-150 | BEA | Powder | 1822-75 |
| 9 | UOP[2] | AlPO$_4$-5 | AFI | Powder | 13551-91-25C |
| 10 | Aldrich[5] | NaX | FAU | Powder | 01820CY |
| 11 | UOP[2] | HiSiv-4000 | Unknown | Powder | 976594061 |
| 12 | Degussa[6] | DAY-55 | FAU | Powder | TC133 |
| 13 | Zeolyst[1] | CBV-901 | FAU | Powder | 1822-66 |
| 14 | UOP[2] | CaA | LTA | Powder | Unknown |
| 15 | Alfa[7] | NaA | LTA | Powder | B12G |

[1]Valley Forge, PA
[2]Des Plaines, IL
[3]Iselin, NJ
[4]Uetikon, Switzerland
[5]Milwaukee, WI
[6]South Plainfield, NJ
[7]Ward Hill, MA Each zeolite (approximately 1 g) was incubated with 4 mL of a soy hey sample in a 10 mL syringe for 15 min. After this time, the mixture was filtered through a 0.2 µm filter and the supernatant was analyzed for sugars using ion chromatography, as described above.

The amount of each sugar adsorbed was determined from the difference in the solution concentration before and after contact with the zeolite and is expressed as a percent in Table 3. As can be seen from the data in the table, only samples 11 (HiSiv-4000) and 13 (CBV-901) adsorbed significant amounts of the undesired oligosaccharides, raffinose and stachyose, in the presence of other sugars. The DAY-55 (sample 12) which was reported to adsorb oligosaccharides (Buttersack et al. Langmuir 12:3101 (1996)), did not adsorb a significant amount of raffinose or stachyose in the presence of the other sugars. This result demonstrates that the adsorption selectivity of this zeolite is different when tested in the presence of other sugars than when tested with a single sugar solution.

TABLE 3

Results of the Adsorption of Sugars by Various Zeolites

| Zeolite | Zeolite Pore Size | Soy Whey Sample | % Glucose Adsorbed | % Fructose Adsorbed | % Sucrose Adsorbed | % Raffinose Adsorbed | % Stachyose Adsorbed |
|---|---|---|---|---|---|---|---|
| 1. Zeolite P | small | 3 | −1 | 13 | 3 | 3 | 4 |
| 2. S-115 | medium | 1 | −7 | Not measured | −2 | −3 | Not measured |
| 3. HiSiv-3000 | medium | 2 | −5 | 21 | −3 | 0 | −1 |
| 4. EZ-500 | medium | 1 | −2 | Not measured | 0 | 0 | Not measured |
| 5. CBV-90A | large | 3 | −9 | −5 | 0 | 0 | 2 |
| 6. ZD-96081 | large | 3 | −1 | 13 | 0 | 0 | 1 |
| 7. Zeocat L | large | 1 | 0 | Not measured | 2 | 5 | Not measured |
| 8. CP-811E-150 | large | 7 | 21 | −34 | 4 | −1 | 4 |
| 9. ALPO$_4$-5 | large | 3 | −6 | 1 | 2 | −1 | 2 |
| 10. NaX | large | 5 | 2 | 9 | −3 | −2 | −2 |
| 11. HiSiv-4000 | large | 2 | 17 | 58 | 64 | 70 | 85 |
| 12. DAY-55 | large | 7 | 2 | −36 | 19 | −8 | −6 |
| 13. CBV-901 | large | 3 | −1 | 16 | 76 | 76 | 96 |
| 14. CaA | small | 5 | 6 | 17 | 1 | 3 | 0.4 |
| 15. NaA | small | 5 | −3 | 0 | −4 | −4 | −3 |

Example 2

Comparative Example of the Adsorption of Sugars by other Adsorbents

The purpose of this Example was to measure the adsorption of sugars from dilute soy whey by other, commonly used adsorbents.

The adsorbents tested are listed in Table 4. The carbon adsorbents (Samples 1 and 2) were used as received. The silica-based adsorbents (Samples 3 and 4) were calcined as described in Example 1.

TABLE 4

List of Adsorbents Used and Their Source

| Adsorbent | Vendor | Product Name | Type | Lot Number |
|---|---|---|---|---|
| 1 | Institute of Technical Carbon[1] | Sibunit #2 | Carbon | unknown |
| 2 | Institute of Technical Carbon[1] | Sibunit #4 | Carbon | unknown |
| 3 | PQ[2] | MA-1030 | Silica | 1676-36-2 |
| 4 | PQ[2] | MS-3050 | Silica | 1902-57-2 |

[1]Omsk, Russia
[2]Valley Forge, PA

These adsorbents were tested for sugar adsorption as described in Example 1 and the results are given in Table 5. As can be seen, none of these adsorbents selectively adsorbed the undesired oligosaccharides, raffinose and stachyose. The carbon adsorbents adsorbed all sugars nonselectively, while the silica adsorbents did not adsorb significant amounts of any of the sugars.

TABLE 5

Adsorption of Sugars by Carbon and Silica Adsorbents

| Adsorbent | Soy Whey Sample | % Glucose Adsorbed | % Fructose Adsorbed | % Sucrose Adsorbed | % Raffinose Adsorbed | % Stachyose Adsorbed |
|---|---|---|---|---|---|---|
| 1 Sibunit #2 | 4 | 63 | 68 | 64 | 62 | 56 |
| 2 Sibunit #4 | 2 | 64 | 90 | 49 | 68 | 63 |
| 3 MA-1030 | 3 | 2 | 13 | 5 | 4 | 5 |
| 4 MS-3050 | 3 | 2 | 9 | 3 | 5 | 5 |

Example 3

Comparative Example of the Selectivity of the Zeolites CBV-901 and DAY-55 in Single Sugar Solutions The purpose of this Example was to compare the selectivity of the zeolites CBV-901 and DAY-55 in the adsorption of sugars from solutions containing single sugars.

A known mass of the dry zeolite sample (typically 0.2-5 g) of either CBV-901 or DAY-55, prepared as described in Example 1, was contacted with a known volume of a sample containing an aqueous solution of either stachyose, raffinose, or sucrose at varying concentrations between 0 and 10 g/L. Samples containing the zeolite were placed on a laboratory rotary shaker (typically set at 200 rpm) and shaken at room temperature for 4-24 h. A portion of the supernatant (typically 1 mL) was withdrawn, filtered, and assayed for sugars using ion chromatography, as described above.

The results for the adsorption of the sugars stachyose, raffinose, and sucrose by the zeolites CBV-901 and Day-55 from single sugar solutions is shown in FIG. 1. In this figure, the amount of each sugar adsorbed by each zeolite in mg/g of zeolite is plotted against the equilibrium sugar concentration. The raw data for this graph is given in Table 6. As can be seen from FIG. 1, CBV-901 is a more effective adsorbent for stachyose and raffinose from single sugar solutions than DAY-55. The adsorption of sucrose was similar for both zeolites.

Example 4

Comparative Example of the Selectivity of the Zeolites CBV-901 and DAY-55 in Multi-Component Sugar Solutions The purpose of this Example was to compare the selectivity of the zeolites CBV-901 and DAY-55 in the adsorption of sugars from solutions containing a mixture of sugars.

The adsorption experiments were done as described in Example 3, except that a sample solution containing an aqueous mixture of the sugars stachyose, raffinose, sucrose, and glucose at varying concentrations between 0 and 3 g/L was used.

Figure 2:
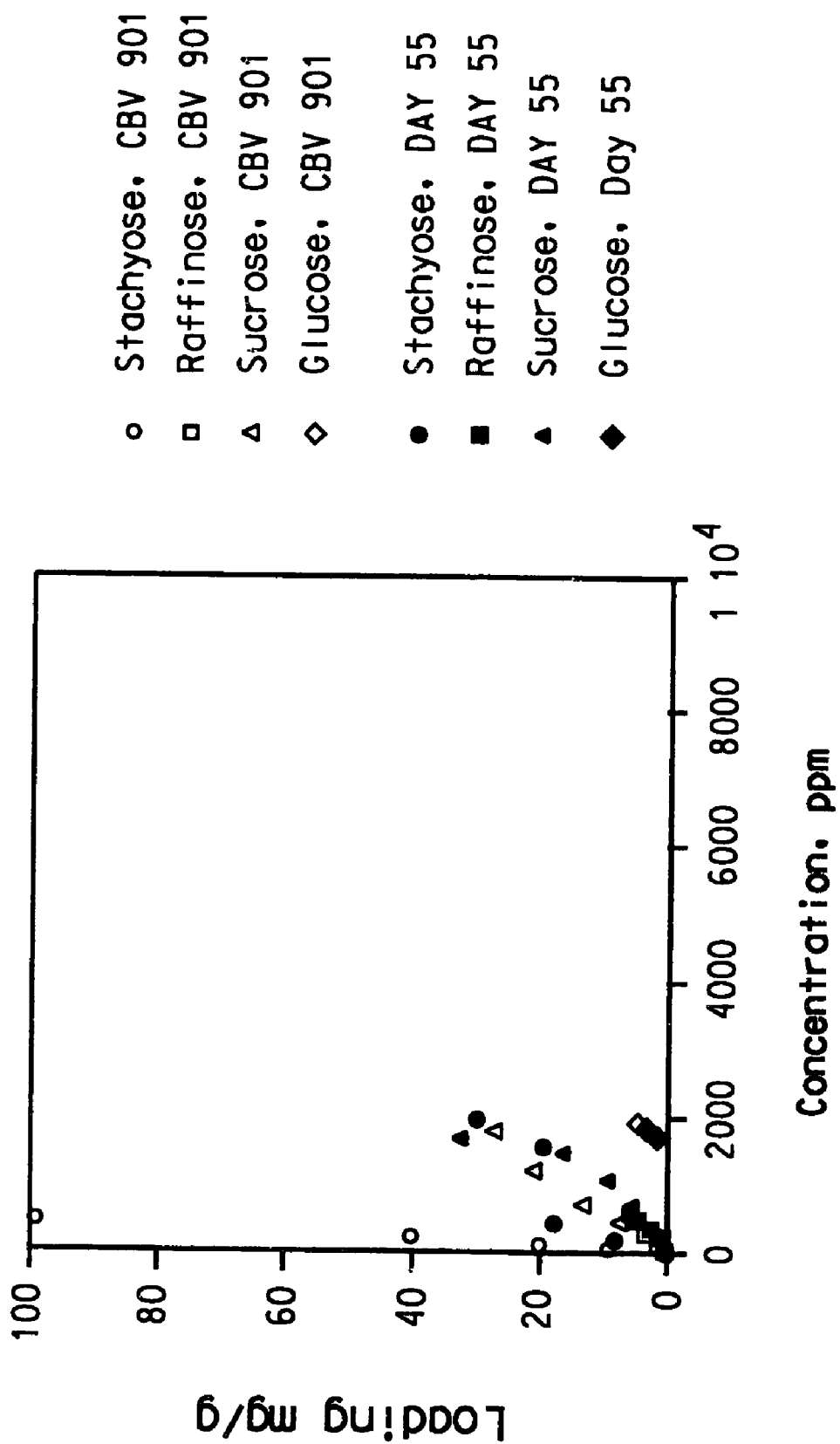
FIG. 2 shows the adsorption of sugars from multi-component sugar solutions by the zeolites CBV-901 and DAY-55.

The results for the adsorption of the sugars stachyose, raffinose, sucrose, and glucose by the zeolites CBV-901 and DAY-55 from multi-component sugar solutions is shown in FIG. 2. In this figure, the amount of each sugar adsorbed from the mixture in mg/g of zeolite is plotted against the equilibrium concentration of each sugar. The raw data for this figure is given in Table 7. As shown in FIG. 2, zeolite CBV-901 is a significantly more effective adsorbent than DAY-55 for the adsorption of the sugars stachyose, raffinose, and sucrose from solutions containing mixtures of the sugars.

TABLE 6

Raw Data for the Adsorption of Sugars from Single Sugar Solutions by Zeolites CBV-901 and DAY-55

| Concentration, ppm | CBV-901 Stachyose Loading, mg/g | CBV-901 Raffinose Loading, mg/g | CBV-901 Sucrose Loading, mg/g | DAY-55 Stachyose Loading, mg/g | DAY-55 Raffinose Loading, mg/g | DAY-55 Sucrose Loading, mg/g |
|---|---|---|---|---|---|---|
| 0.0 | 0.0 | 0.0 | 0.0 | 0.0 | 0.0 | 0.0 |
| 1904.3 | 83.9 | — | — | — | — | — |
| 4405.5 | 296.3 | — | — | — | — | — |
| 5081.1 | 518.4 | — | — | — | — | — |
| 1532.2 | — | −4.4 | — | — | — | — |
| 2192.5 | — | 47.2 | — | — | — | — |
| 4191.2 | — | 141.0 | — | — | — | — |
| 7069.7 | — | 676.5 | — | — | — | — |
| 2181.5 | — | — | 22.1 | — | — | — |
| 4532.5 | — | — | 47.6 | — | — | — |
| 5898.5 | — | — | 204.6 | — | — | — |
| 2802.7 | — | — | — | −6.0 | — | — |
| 5448.7 | — | — | — | 192.0 | — | — |
| 6707.2 | — | — | — | 355.8 | — | — |
| 1416.4 | — | — | — | — | 18.7 | — |
| 2775.9 | — | — | — | — | −69.5 | — |
| 4325.0 | — | — | — | — | 127.7 | — |
| 9569.7 | — | — | — | — | 426.5 | — |
| 2347.5 | — | — | — | — | — | 5.5 |
| 4570.2 | — | — | — | — | — | 43.9 |
| 5307.8 | — | — | — | — | — | 263.7 |

TABLE 7

Raw Data for the Adsorption of Sugars from Multicomponent Sugar Solutions by the Zeolites CBV 901 and Day-55

| Conc., ppm | CBV-901 Stachyose Loading, mg/g | CBV-901 Raffinose Loading, mg/g | CBV-901 Sucrose Loading, mg/g | CBV-901 Glucose Loading, mg/g | DAY-55 Stachyose Loading, mg/g | DAY-55 Raffinose Loading, mg/g | DAY-55 Sucrose Loading, mg/g | DAY-55 Glucose Loading, mg/g |
|---|---|---|---|---|---|---|---|---|
| 620.4 | 98.5 | — | — | — | — | — | — | — |
| 192.9 | 40.0 | — | — | — | — | — | — | — |
| 128.7 | 20.5 | — | — | — | — | — | — | — |
| 87.4 | 10.4 | — | — | — | — | — | — | — |
| 0.0 | 0.0 | — | — | — | — | — | — | — |
| 488.8 | — | 6.4 | — | — | — | — | — | — |
| 305.8 | — | 5.2 | — | — | — | — | — | — |
| 211.2 | — | 3.4 | — | — | — | — | — | — |
| 132.4 | — | 2.0 | — | — | — | — | — | — |
| 0.0 | — | 0.0 | — | — | — | — | — | — |
| 1839.1 | — | — | 26.7 | — | — | — | — | — |
| 1081.5 | — | — | 21.5 | — | — | — | — | — |
| 683.0 | — | — | 14.1 | — | — | — | — | — |
| 383.7 | — | — | 8.3 | — | — | — | — | — |
| 0.0 | — | — | 0.0 | — | — | — | — | — |
| 1829.0 | — | — | — | 2.9 | — | — | — | — |
| 1797.9 | — | — | — | 1.5 | — | — | — | — |
| 1732.2 | — | — | — | 1.3 | — | — | — | — |
| 1724.6 | — | — | — | 0.7 | — | — | — | — |
| 0.0 | — | — | — | 0.0 | — | — | — | — |
| 1988.5 | — | — | — | — | 30.1 | — | — | — |
| 1381.7 | — | — | — | — | 20.2 | — | — | — |
| 432.7 | — | — | — | — | 18.0 | — | — | — |
| 200.9 | — | — | — | — | 10.0 | — | — | — |
| 0.0 | — | — | — | — | 0.0 | — | — | — |
| 478.9 | — | — | — | — | — | 6.9 | — | — |
| 390.5 | — | — | — | — | — | 3.8 | — | — |
| 296.7 | — | — | — | — | — | 2.7 | — | — |
| 198.9 | — | — | — | — | — | 1.7 | — | — |
| 0.0 | — | — | — | — | — | 0.0 | — | — |
| 1732.1 | — | — | — | — | — | — | 32.0 | — |
| 1340.5 | — | — | — | — | — | — | 17.2 | — |
| 976.7 | — | — | — | — | — | — | 11.6 | — |
| 599.2 | — | — | — | — | — | — | 7.4 | — |
| 0.0 | — | — | — | — | — | — | 0.0 | — |
| 1740.3 | — | — | — | — | — | — | — | 7.3 |
| 1777.1 | — | — | — | — | — | — | — | 1.8 |
| 1690.3 | — | — | — | — | — | — | — | 1.6 |
| 1633.2 | — | — | — | — | — | — | — | 1.1 |
| 0.0 | — | — | — | — | — | — | — | 0.0 |

Example 5

Comparative Example of the Selectivity of the Zeolites CBV-901 and DAY-55 in Dilute Soy Whey Solution The purpose of this Example was to compare the selectivity of the zeolites CBV-901 and DAY-55 in the adsorption of sugars from dilute soy whey solutions.

The adsorption experiments were done as described in Example 3, except that the sample solution was dilute soy whey.

Figure 3:
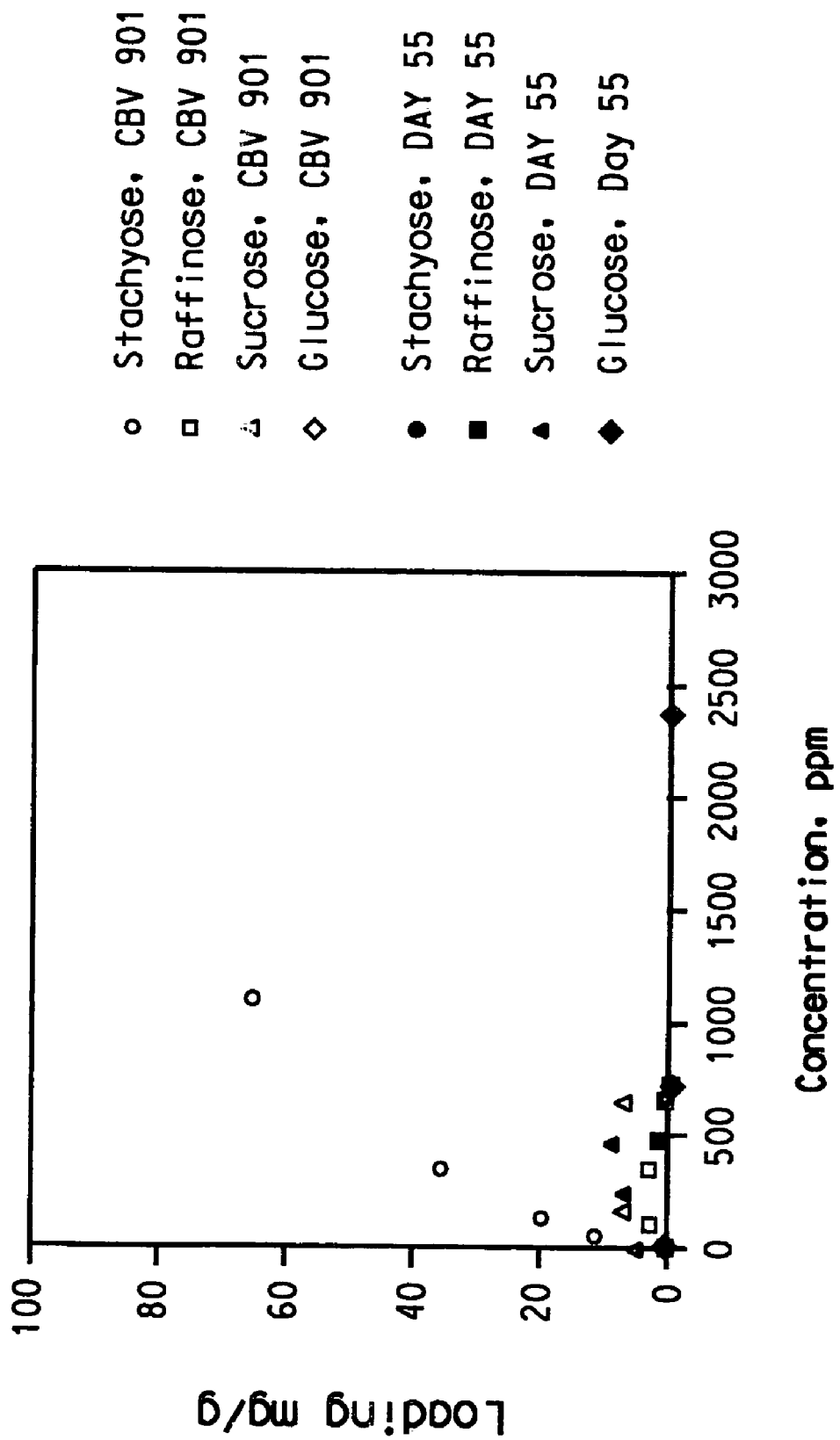
FIG. 3 shows the adsorption of sugars from dilute soy whey by the zeolites CBV-901 and DAY-55.

The results for the adsorption of the sugars stachyose, raffinose, sucrose, and glucose by the zeolites CBV-901 and DAY-55 from dilute soy whey is shown in FIG. 3. In this figure, the amount of each sugar adsorbed by each zeolite in mg/g of zeolite is plotted against the equilibrium concentration of the sugar. The raw data for this figure is given in Table 8. As shown in this figure, the difference in adsorption of the sugars by the two zeolites is even more marked in the presence of dilute soy whey. There was relatively little adsorption of any sugar other than sucrose by Day-55, while CBV-901 adsorbed significant amounts of stachyose and some sucrose and raffinose. These results demonstrate the superior selectivity of CBV-901 for removing the undesired sugars stachyose and raffinose from soy whey.

TABLE 8

Raw Data for the Adsorption of Sugars from Dilute Soy Whey by the Zeolites CBV-901 and DAY-55

| Conc., ppm | CBV-901 Stachyose Loading, mg/g | CBV-901 Raffinose Loading, mg/g | CBV-901 Sucrose Loading, mg/g | CBV-901 Glucose Loading, mg/g | DAY-55 Stachyose Loading, mg/g | DAY-55 Raffinose Loading, mg/g | DAY-55 Sucrose Loading, mg/g | DAY-55 Glucose Loading, mg/g |
|---|---|---|---|---|---|---|---|---|
| 1084.0 | 65.7 | — | — | — | — | — | — | — |
| 358.0 | 35.2 | — | — | — | — | — | — | — |
| 161.0 | 20.3 | — | — | — | — | — | — | — |
| 55.0 | 13.1 | — | — | — | — | — | — | — |
| 612.0 | — | 0.3 | — | — | — | — | — | — |
| 318.0 | — | 2.6 | — | — | — | — | — | — |
| 112.0 | — | 2.6 | — | — | — | — | — | — |
| 1118.0 | — | — | −6.3 | — | — | — | — | — |
| 589.0 | — | — | 5.8 | — | — | — | — | — |
| 171.0 | — | — | 6.5 | — | — | — | — | — |
| 0.0 | — | — | 4.9 | — | — | — | — | — |
| 2931.0 | — | — | — | −4.6 | — | — | — | — |
| 1820.0 | — | — | — | 2.8 | — | — | — | — |
| 2785.0 | — | — | — | — | −2.1 | — | — | — |
| 2754.0 | — | — | — | — | −0.9 | — | — | — |
| 2668.0 | — | — | — | — | −0.1 | — | — | — |
| 627.0 | — | — | — | — | — | 0.1 | — | — |
| 563.0 | — | — | — | — | — | 0.6 | — | — |
| 430.0 | — | — | — | — | — | 1.0 | — | — |
| 450.0 | — | — | — | — | — | — | 8.1 | — |
| 229.0 | — | — | — | — | — | — | 6.3 | — |
| 0.0 | — | — | — | — | — | — | 4.7 | — |
| 2461.0 | — | — | — | — | — | — | — | −1.4 |
| 2365.0 | — | — | — | — | — | — | — | 0.1 |
| 2400.0 | — | — | — | — | — | — | — | −0.1 |

What is claimed is:

1. A method for selectively removing the oligosaccharides raffinose and stachyose from an aqueous mixture comprising said oligosaccharides raffinose and stachyose, and digestible sugars, the method comprising the steps of:
    (a) contacting the aqueous mixture with an ultrastabilized hydrophobic zeolite Y having a Si/Al ratio of about 10 to about 45, whereby at least a portion of said oligosaccharides bind to said ultrastabilized hydrophobic zeolite and is selectively removed from the aqueous mixture, thereby forming a treated aqueous mixture having an increased proportion of the digestible sugars relative to the oligosaccharides;
    (b) separating the ultrastabilized hydrophobic zeolite Y from the treated aqueous mixture; and
    (c) recovering the treated aqueous mixture.

2. A method of using an ultrastabilized hydrophobic zeolite Y having a Si/Al ratio of about 10 to about 45 for selectively removing the oligosaccharides raffinose and stachyose from an aqueous mixture comprising said oligosaccharides raffinose and stachyose, and digestible sugars, the method comprising the steps of:
    (a) contacting the aqueous mixture with said ultrastabilized hydrophobic zeolite Y, whereby at least a portion of said oligosaccharides bind to said ultrastabilized hydrophobic zeolite Y and is selectively removed from the aqueous mixture, thereby forming a treated aqueous mixture having an increased proportion of the digestible sugars relative to the oligosaccharides;
    (b) separating the ultrastabilized hydrophobic zeolite Y from the treated aqueous mixture; and
    (c) recovering the treated aqueous mixture.

3. The method of claim 1 or claim 2 wherein the aqueous mixture is a plant processing waste product.

4. The method of claim 3 wherein the plant processing waste product is soy whey.

5. The method of claim 1 or claim 2 wherein the zeolite is used in a batch reactor.

6. The method of claim 1 or claim 2 wherein the zeolite is used in a column.

7. The method of claim 1 or claim 2 wherein steps a or b, or a and b, are repeated one or more times.

8. The method of claim 1 or claim 2 further comprising the steps of recovering the raffinose and stachyose from the zeolite, and hydrolyzing them into simple sugars.

* * * * *